US00PP08095P

United States Patent [19]

VandenBerg

[11] Patent Number: Plant 8,095

[45] Date of Patent: Jan. 12, 1993

[54] CHRYSANTHEMUM PLANT NAMED YELLOW ILLUSION

[75] Inventor: Cornelis P. VandenBerg, Salinas, Calif.

[73] Assignee: Yoder Brothers, Inc., Barberton, Ohio

[21] Appl. No.: 650,941

[22] Filed: Feb. 5, 1991

[51] Int. Cl.[5] ..... A01H 5/00

[52] U.S. Cl. ..... Plt./74.1

[58] Field of Search ..... Plt./74, 74.1, 78, 82.1, Plt./82.2

[56] References Cited

U.S. PATENT DOCUMENTS

P.P. 6,644 2/1989 Mack et al. ..... Plt. 74

4,616,099 10/1986 Sparkes ..... 800/200

*Primary Examiner*—James R. Feyrer

*Attorney, Agent, or Firm*—Foley & Lardner

[57] ABSTRACT

A Chrysanthemum plant named Yellow Illusion particularly characterized by its flat capitulum form; spooned daisy capitulum type; light yellow ray floret color; diameter across face of capitulum of 80 to 85 mm when fully opened; spreading and prolific branching pattern, with 7 breaks after pinch when grown outside under natural daylength in fall flowerings, and 5 to 7 breaks after pinch when grown in 10 cm pots for spring flowerings; natural season flowering date of August 29 when planting rooted cuttings June 23 in Salinas, Calif., and October 3 when planting rooted cuttings June 12 in Hightstown, N.J.; flowering response of 46 days after rooting in no light/no shade programs in spring; plant height of 33 cm when grown in fall under natural daylength with no growth regulators, and of 28 cm when grown in 10 cm pots in spring with 1 application of 2500 ppm B-9 SP; and durable, uniform performance.

1 Drawing Sheet

The present invention comprises a new and distinct cultivar of Chrysanthemum, botanically known as *Dendranthema grandiflora,* and referred to by the cultivar name Yellow Illusion.

Yellow Illusion, identified as 84-M23C04, is a product of a mutation induction program. The new cultivar was discovered and selected by Cornelis P. VandenBerg on Jul. 20, 1987 in a controlled environment in Salinas, Calif., as one flowering plant within a flowering block established as rooted cuttings from stock plants which had been exposed as unrooted cuttings to an X-ray source of 1750 rads. The irradiated parent cultivar was Illusion, a white flat spooned daisy spray pot mum and garden mum, disclosed in U.S. Plant Pat. No. 6,644.

The irradiation program resulting in Yellow Illusion had as its primary objective the expansion of color ranges of Illusion, which is white in ray floret color. The program comprised irradiating cuttings of the parent cultivar Illusion at irradiation levels of 1500, 1750 and 2000 rads. A total of 718 cuttings harvested from a total of 225 irradiated plants were planted on April 20, May 11 and May 25, 1987. Of these, 14 initial selections were made, which selections were then revegetated and reflowered. Four consecutive flowerings resulted in discarding 10 of the original 14 selections on Apr. 4, 1988. Four selections were retained to be further tested as possible introductions in our natural season flowering programs in Salinas, Calif. and in Hightstown, N.J. These flowerings resulted in discarding three out of the four selections on Sep. 28, 1989, and the decision to commercially introduce the one remaining selection as Yellow Illusion. Although color expansion was the objective of the program, the induced mutation Yellow Illusion distinguishes from the parent cultivar Illusion in other respects as well, as will be noted.

The first act of asexual reproduction of Yellow Illusion was accomplished when vegetative cuttings were taken from the initial selection in September 1987 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Illusion are firmly fixed and are retained through successive generations of asexual reproduction.

Yellow Illusion has not been observed under all possible environmental conditions. The phenotype may vary significantly with variations in environment such as temperature, light intensity and daylength.

The following observations, measurements and comparisons describe plants grown in controlled open areas in Salinas, Calif. and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Yellow Illusion, which, in combination, distinguish this Chrysanthemum as a new and distinct cultivar:

1. Flat capitulum form.
2. Spooned daisy capitulum type.
3. Light yellow ray floret color.
4. Diameter across face of capitulum of 80 to 85 mm when fully opened.
5. Branching pattern is spreading and prolific, with 7 breaks after pinch when grown outside under natural daylength in fall flowerings, and 5 to 7 breaks after pinch when grown in 10 cm pots for spring flowerings.
6. Natural season flower date of August 29 when planting rooted cuttings on June 23 in Salinas, Calif., and of October 3 when planting rooted cuttings June 12 in Hightstown, N.J.

7. Flowering response of 46 days after rooting in no light/no shade programs in spring.

8. Plant height of 33 cm when grown in fall under natural daylength with no growth regulators, and of 28 cm when grown in 10 cm pots in spring with 1 application of 2500 ppm B-9 SP.

9. Durable, uniform performance.

The accompanying photographic drawing is a color photograph of Yellow Illusion grown as a pinched pot mum with four cuttings in a 15 cm pot, with the colors being as nearly true as possible with illustrations of this type.

Of the commercial cultivars known to the inventor, the most similar in comparison to Yellow Illusion is the parent cultivar Illusion. Most traits of Yellow Illusion are similar to those of Illusion, except ray floret color, vigor and response. The flower color of Yellow Illusion is a light yellow, while the flower color of Illusion is white. In several of our flowering trails Yellow Illusion had slightly less vigor by 2.5 to 5 cm than Illusion.

The spring response for Illusion is 45 days compared to 46–47 days for Yellow Illusion. The natural flowering dates in New Jersey for Illusion is September 23 to October 3, compared to September 30 to October 3 for Yellow Illusion, based on rooted cuttings planted at the same time. The flowering dates in Salinas, Calif. for Illusion is August 27–31 and for Yellow Illusion August 29 to September 1.

In the following description color references are made to The Royal Horticultural Society Colour Chart. The color values were determined on plant material grown as a pinched spray pot mum in Salinas, Calif. on May 2, 1990.

Classification:

*Botanical.*—*Dendranthema grandiflora* cv Yellow Illusion.

*Commercial.*—Flat spooned daisy spray pot mum and garden mum.

INFLORESCENCE

A. Capitulum:

*Form.*—Flat.

*Type.*—Spooned daisy.

*Diameter across face.*—80 to 85 mm when fully opened.

B. Corolla of ray florets:

*Color (general tonality from a distance of three meters).*—Light yellow.

*Color (outside tube).*—8B to 8C.

*Color (inside tube).*—8A to 8B.

*Shape.*—Spooned, with very small spoons. Many ray florets are quilled and needle-like.

C. Corolla of disc florets:

*Color (mature).*—13B to 14B.

*Color (immature).*—151C, tinged with 144B.

D. Reproductive organs:

*Androecium.*—Present on disc florets only; moderate pollen.

*Gynoecium.*—Present on both ray and disc florets.

PLANT

A. General appearance:

*Height.*—33 cm when grown in fall under natural daylength with no growth regulators, and of 28 cm when grown in 10 cm pots in spring with 1 application of 2500 ppm B-9 SP.

*Branching pattern.*—Spreading and prolific, with 7 breaks after pinch when grown outside under natural daylength in fall flowerings, and 5 to 7 breaks after pinch when grown in 10 cm pots for spring flowerings.

B. Foliage:

*Color (upper surface).*—147A.

*Color (under surface).*—147B.

*Shape.*—Lobed and slightly serrated.

I claim:

1. A new and distinct Chrysanthemum plant named Yellow Illusion, as described and illustrated.

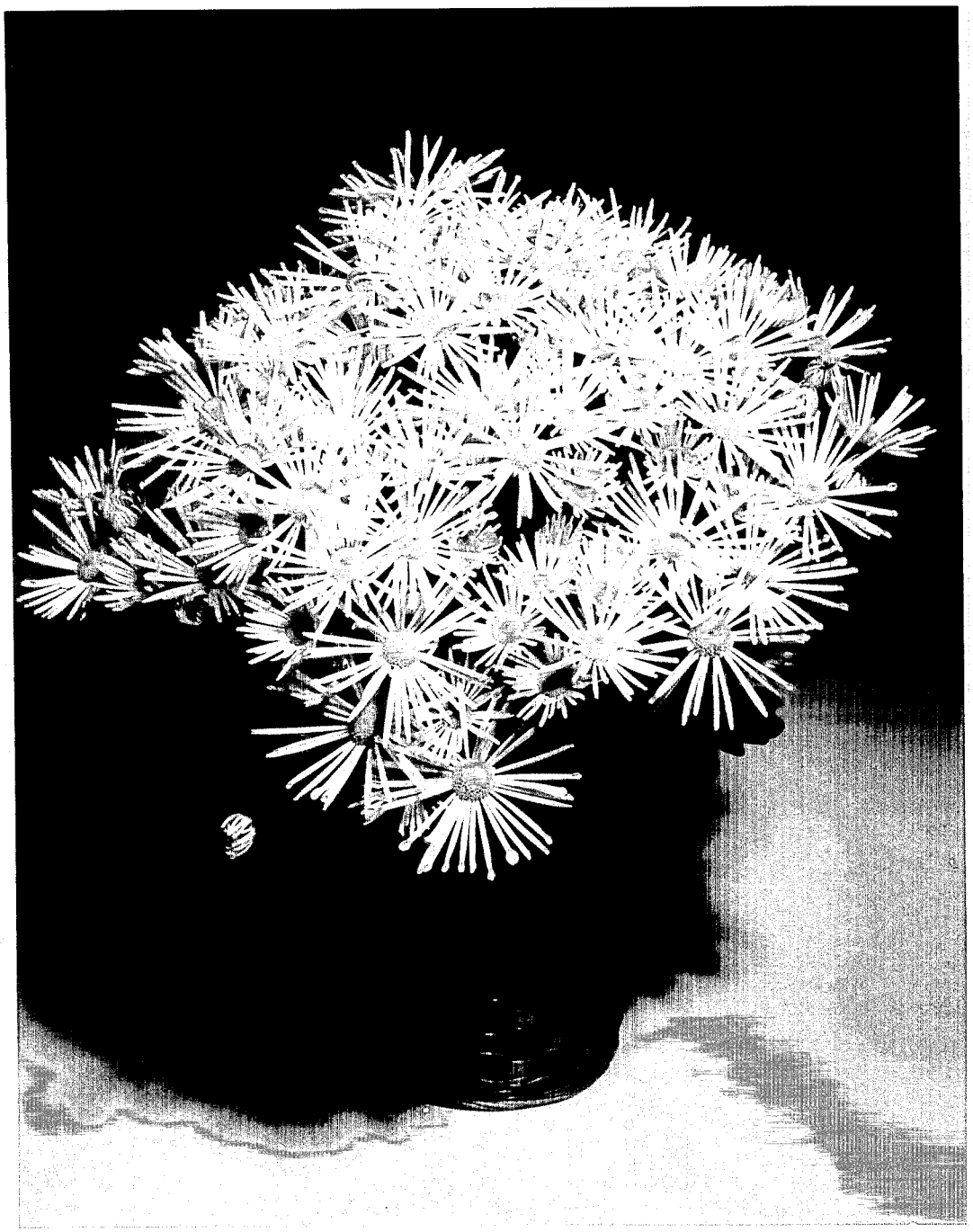

* * * * *